United States Patent [19]

Schade

[11] Patent Number: 5,304,634

[45] Date of Patent: Apr. 19, 1994

[54] INHIBITORS FOR THE FORMATION OF TUMOR NECROSIS FACTOR

[75] Inventor: Ulrich F. Schade, Wardersee, Fed. Rep. of Germany

[73] Assignee: Hoechst Aktiengesellschaft, Frankfurt am Main, Fed. Rep. of Germany

[21] Appl. No.: 773,502

[22] Filed: Oct. 9, 1991

[30] Foreign Application Priority Data

Oct. 12, 1990 [DE] Fed. Rep. of Germany ....... 4032354

[51] Int. Cl.$^5$ .................. C07K 3/00; C07K 15/00; A01N 37/18; C12P 21/02
[52] U.S. Cl. .................. 530/350; 530/351; 435/701; 435/240.2
[58] Field of Search ............. 435/70.1, 240.2; 530/351, 350, 397, 399; 514/12, 2

[56] References Cited

U.S. PATENT DOCUMENTS 5,055,447 10/1991 Palladino et al. ............... 514/12

FOREIGN PATENT DOCUMENTS 0308378 3/1989 European Pat. Off. .
0422339A1 4/1991 European Pat. Off. .
2218101 8/1989 United Kingdom .......... C07K 3/28

OTHER PUBLICATIONS

Tracey et al. (1987) Nature vol. 330, pp. 662–664.
Band et al. (1989) Kidney Int. (USA) 35/5, pp. 1111–1118.
Kujawa et al. (1989) Naval Medical Research Inst., Bethesda, Md., Report No.:NMRI-89-7.
Seckinger et al. (1988) J. Exp. Med., vol. 167, pp. 1511–1516.
Andrews et al. (Apr. 1, 1990) The Journal of Immunology, vol. 144, pp. 2582–2591.
Gupta, "Cytokines: Molecular and Biological Characteristics", Scand. J. Rheumatology (1988), Suppl. 76, pp. 189–201.
Tracey et al., "Shock and Tissue Injury Induced by Recombinant Human Cachectin", Science, vol. 234 (Oct. 24, 1986), pp. 470–474.
Tracey et al., "Anti-Cachectin/TNF Monoclonal Anti7 bodies Prevent Septic Shock During Lethal Bacteraemia", Nature, vol. 330 (Dec. 17, 1987), pp. 662–664.
Zabel et al., "Oxpentifylline in Endotoxaemia", The Lancet (Dec. 23/30, 1989), pp. 1474–1477.
Essner et al., "IL-4 Down-Regulates IL-1 and TNF Gene Expression in Human Monocytes", J. Immunol., vol. 142 (Jun. 1, 1989), pp. 3857–3861.
U. Schade et al., "Differences In Lipopolysaccharide-Induced Prostaglandin-Release And Phagocytic Activity Of Peritoneal Macrophages From LPS-Hyperreactive And Tolerant Mice," Natural Toxins, pp. 271–277 (D. Baker et al. eds., 1980).
Roitt et al., Immunology (New York, Gower Medical Publishing), pp. 2.8–2.11, 5.1–5.5.

Primary Examiner—Robert J. Hill, Jr.
Assistant Examiner—Gian P. Wang
Attorney, Agent, or Firm—Finnegan, Henderson, Farabow, Garret & Dunner

[57] ABSTRACT

The invention relates to inhibitors for the formation of tumor necrosis factor, processes for the preparation thereof by macrophages or mononuclear phagocytes which have been stimulated by lipopolysaccharides, and the use thereof for the treatment and prophylaxis of diseases caused by tumor necrosis factor.

3 Claims, No Drawings

INHIBITORS FOR THE FORMATION OF TUMOR NECROSIS FACTOR

BACKGROUND OF THE INVENTION

1. Field of the Invention

The invention relates to inhibitors for the formation of tumor necrosis factor, processes for the preparation thereof by macrophages or mononuclear phagocytes which have been stimulated by lipopolysaccharides, and the use thereof for the treatment and prophylaxis of diseases caused by tumor necrosis factor.

Inflammatory reactions primarily come about by over-expression of immunological mechanisms which are originally present to protect the host organism. It has become clear in recent years that proteins which are formed by the host may in isolated form cause symptoms of disease by bringing about the release of terminal mediators of inflammation. This class of hormone-like proteins is embraced by the term cytokines (Gupta, Scand J Rheumatol Suppl. , (1988) 76, 189). It is now regarded as certain that cytokines are of fundamental importance for the development of inflammatory processes.

2. Description of the Related Art

Among the cytokines, tumor necrosis factor (TNF) has achieved particular importance for the development of acute inflammatory processes because this substance, which is essentially formed by macrophages, is able to induce in mammals a state of shock as is characteristic of bacteremias and sepsis (Tracey et al. Science, 234, (1986), 470). It has furthermore been found that a monoclonal antibody against TNF suppresses lethality in monkeys during bacterial sepsis (Tracey et al., Nature, 330, (1987), 662). It is evident from these findings that TNF is, on the one hand, a sufficient and, on the other hand, an essential factor for the development of many characteristics of endotoxic shock.

The evident linkage between endogenous TNF formation and the development of acute and chronic inflammatory syndromes has led to many attempts to block the endogenous formation of TNF by pharmacological inhibitors. Mention may be made here by way of example of the treatment with steroids, xanthine derivatives and lipoxygenase inhibitors (Zabel et al., Lancet, 23, (1989), 1474). It has also emerged that the cytokine IL 4 is an inhibitor of TNF formation (Essner et al., J. Immunol. 142, (1989), 3857).

The object of the invention was to find new physiological inhibitors with which the endogenous formation of TNF can be inhibited.

SUMMARY OF THE INVENTION

It has now been found, surprisingly, that macrophages or mononuclear phagocytes are able to produce inhibitors of the formation of TNF.

Thus the invention relates to:

1. Inhibitors of the formation of tumor necrosis factor, obtainable by cultivation of macrophages or mononuclear phagocytes from lipopolysaccharide-tolerant vertebrates, called TNFI (for Tumor Necrosis Factor Inhibitor) hereinafter.
2. A process for preparing the inhibitor characterized under 1., which comprises cultivating macrophages or mononuclear phagocytes from lipopolysaccharide-tolerant vertebrates and subsequently adding lipopolysaccharides to the latter.
3. The use of the inhibitor characterized under 1. for preparing a medicoment for the treatment or prophylaxis of diseases caused by tumor necrosis factor.

Lipopolysaccharide (LPS) means cell wall components of Gram-negative bacteria. They are composed of a lipoid A and various polysaccharides which can contain various sugar components depending on the bacterial species. LPS acts as an endotoxin, may induce fever, leukopenia and leukocytosis, and brings about a local Schwarzmann reaction in rabbits. For example, a lipopolysaccharide can be extracted from Salmonella friedenau by the phenol-water method, and be lyophilized and converted into the triethylamine salt form (Galanos et al., Zentralbl. Bakteriol. Parasitenkd. Infektionskd. Hyg. Abt. 1: Orig. Reihe A: 243, (1979), 226). Tumor necrosis factor (TNF) is a cytokine which is formed, in particular, by macrophages and has lytic activity on certain transformed cell lines.

IL4 is a B-cell growth factor which acts to activate macrophages and has a molecular weight of 15,000 to 20,000. IL 6 is a B-cell differentiation factor which acts as growth factor on hybridoma cell lines and has a molecular weight between 22,000 and 34,000.

DESCRIPTION OF THE PREFERRED EMBODIMENTS

The TNF inhibitor according to the invention is a product whose characteristics may be said to be as follows:

- has a molecular weight between 40,000 and 80,000
- inhibits the synthesis of TNF by macrophages
- does not act like interleukin IL 6 as growth factor for hybridoma cell lines The inhibitor is produced, for example, by macrophages which can be obtained from lipopolysaccharide-tolerant vertebrates. Suitable examples are macrophages obtained from lipopolysaccharide-tolerant NMRI mice or C3H/HEJ mice (NMRI stands for Naval Medical Research Institute). Furthermore, human mononuclear phagocytes can also be used to produce inhibitors according to the invention.

The best procedure for preparing the inhibitor according to the invention is first to induce an LPS tolerance in the vertebrates. Thus, for example, female NMRI mice (6–8 weeks, Lippische Versuchstieranstalt, Dextertal, Germany) can be made tolerant to LPS by an intraperitoneal injection of about 80 $\mu$g of LPS, obtained from Salmonella friedenau by the phenol-water method, in 200 $\mu$l of pyrogen-free buffer. After 96 hours, the mice are in the state of LPS tolerance, which is indicated by none of the tolerant animals dying on injection of 2 mg of LPS/mouse. In normal mice 0.7 mg of the LPS used corresponds to one $LD_{100}$.

Peritoneal macrophages are obtained from the LPS-tolerant mice by methods disclosed in the literature (Conrad, Manual of macrophage methodology. Ed. Herscowitz et al. (1981)). The isolated macrophages are transferred into sterile cultivation vessels and subsequently incubated in known cultivation media for mammalian cells, cell lines and tissue cultures in a $CO_2$ incubator for 2 to 3 hours. The cultivation medium is removed, non-adherent cells are washed off with buffer, fresh medium is added and stimulation is carried out with LPS.

The amounts of LPS stated hereinafter relate to the LPS from Salmonella friedenau which has been obtained by the phenol-water method. The macrophages are induced with about 1 to 100 μg of LPS/ml of medium, preferably 5 to 60 μg/ml. The macrophages are cultivated in a $CO_2$ incubator at 37° C. and 8% $CO_2$. The macrophages release the inhibitor according to the invention into the surrounding medium. The maximum inhibitor concentration is reached 15 to 36 hours after induction. The macrophages are removed from the medium, for example by centrifugation or filtration. The inhibitors according to the invention remain in the medium from which they can be obtained by conventional methods of protein concentration. Other methods disclosed in the literature for the cultivation of cell lines can likewise be used. It has proven advantageous to induce the macrophages again with LPS after the first synthesis of TNFI and to bring about further TNFI production with fresh cultivation medium. Thus, it has been possible to observe production of TNFI over one week.

Furthermore, TNFI can also be produced by macrophages from C3H/HeJ mice (Bomholtghrd Ltd., Denmark). In this case no treatment of the mice with LPS was carried out. The peritoneal macrophages are isolated and induced with LPS, and TNFI is isolated, as described for the NMRI mice.

Another method for preparing the inhibitor according to the invention comprises obtaining it from human mononuclear phagocytes. The best procedure for this is initially to generate LPS tolerance in human subjects. It is possible for this purpose to inject, for example, 100 ng of Salmonella abortus equi intravenously. 3 days after induction, 50 ml of blood are taken and from this mononuclear phagocytes (monocytes) are obtained by methods disclosed in the literature. The cells can be isolated, for example, via a ®Percoll gradient. T isolated monocytes ($1 \times 10^6$ cells/ml of medium) are subsequently incubated in culture media disclosed in the literature for mammalian cells, cell lines and tissue cultures with customary cultivation conditions for 2 to 3 hours. Inhibitor synthesis is induced with LPS. For this, 1 to 100 μg/ml of medium, preferably 5 to 60 μg/ml, are added to the medium, and the monocytes are cultivated under the same cultivation conditions as the macrophages from LPS-tolerant mice, and subsequently TNFI is isolated.

The characteristic action of the inhibitor can be demonstrated by its action on the synthesis of TNF by macrophages. The action of the inhibitors according to the invention can be determined, for example, by the cell line RAW 264.7 (American Type Culture Collection 71 TIB (ATCC), Maryland, USA). This cell line forms TNF after stimulation by LPS. The formation of TNF in this cell line can be inhibited by solutions containing TNFI.

EXAMPLE 1

Female NMRI mice (6–8 weeks, Lippische Versuchstieranstalt, Dextertal, Germany) are made tolerant to LPS by an intraperitoneal injection of about 80 μg of LPS, obtained from Salmonella friedenau by the phenol-water method, in 200 μl of pyrogen-free buffer. After 96 hours, the mice are in the state of LPS tolerance, which is indicated by none of the tolerant animals dying on injection of 2 mg of LPS/mouse. In normal mice, 0.7 mg of the LPS used corresponds to one $LD_{100}$. The peritoneal macrophages are obtained from the LPS-tolerant mice. For this, the mice are sacrificed by exposure to $CO_2$, fixed to a cork plate and sprayed with 70% alcohol. Then, in a sterile workbench the skin is opened by an incision in the belly and abdominal region, and 5 ml of irrigation medium (Iscove's medium + 2.5 U/ml heparin; Sigma) are injected into the peritoneal cavity. The peritoneum which has been filled in this way is cautiously massaged in order to detach cells adhering to tissue. A sterile Pasteur pipette is used to aspirate out the liquid containing the cells. An amount of liquid containing 107 cells is pipetted into a cell culture dish and incubated with culture medium (Iscove's Medium, 2 h, 37° C., 8% $CO_2$). In order to purify the macrophage cultures of contaminating cell types, the supernatants are removed from the adherent cells, and the cells are washed twice with 10 ml of buffer each time (37° C.) and covered with 10 ml of fresh Iscove's medium. Then 50 μg/ml of LPS are added per ml of medium The LPS used is isolated from Salmonella friedenau by the phenol-water method. The macrophages are cultivated in a $CO_2$ incubator at 37° C. and 8% $CO_2$. The macrophages release the inhibitor according to the invention into the surrounding medium. The maximum inhibitor concentration is reached 15 to 36 hours after induction. The cell culture supernatants are centrifuged ($1000 \times g$). The macrophages sediment and the inhibitor remains in the medium. The produced TNFI concentration is determined by the action of TNFI on the TNF production by the cell line RAW 264.7 (ATCC 71 TIB). The amount of inhibitor contained in the medium reduces the synthesis of TNF by RAW 264.7 to 30% of the control.

TNF induction: RAW 264.7 cells are pipetted into microtiter plates filled with Iscove's medium (Iscove medium with 10% fetal calf serum (FCS); Gibco/BRL, Eggenstein, FRG). The cell concentration is adjusted to about $1 \times 10^6$ cells/ml of medium. After 2 h, the cells are washed with buffer, covered with fresh medium and incubated with 200 ng of LPS/ml in the presence of TNFI. Serum-free Iscove's medium is used. After an incubation time of 18 h, the supernatants are obtained and stored at −70° until TNF is determined.

Determination of TNF: the TNF is determined in a bioassay with the ATCC fibroblast cell line L929. The cells are pipetted into 100 μl of culture medium (RPMI 1640 + 10% FCS + 5 μg/ml actinomycin; Gibco) in 96-well plates ($2 \times 10^4$ cells/well; flat-bottomed). The cells are incubated at 37° C. with 5% $CO_2$ in the air for 4 h. Then 100 μl of each of the serial dilutions of the samples to be tested are pipetted onto the cells. These mixtures are incubated under the same conditions for 18 h and then, after addition of 10 μl of a solution of 5 mg/ml MTT (MTT=3-(4,5-dimethylthiazol-2-yl)-2,5-diphenyltetrazolium bromide; dissolved in buffer; Sigma, Deisenhofen)/100 μl of culture medium, incubated for a further 4 h.

After this the supernatants are discarded and replaced by 100 μl of 0.04N HCl in isopropanol. After shaking vigorously, the absorptions at 570 nm are measured using an ELISA reader (MR 700, Dynatech Laboratories). The TNF titer of the sample was calculated using the following formula:

$$\% \text{ cytotoxicity} = \frac{A_{con} - A_{dil}}{A_{con}} \times 100$$

$A_{con}$ is the absorption of the control. $A_{dil}$ is the absorption of the wells with the TNF-containing dilutions. One unit of TNF is defined as the reciprocal of that dilution at which 50% lysis is reached.

EXAMPLE 2

Dose-Dependence of the Induction

Peritoneal macrophages are prepared from LPS-tolerant mice as described in Example 1 ($1 \times 10^6$ cells/ml) and incubated in vitro with various LPS doses (18 hr, 37° C., 8% $CO_2$). The inhibitor activity from the resulting supernatants is determined.

The macrophages from LPS-tolerant mice require in vitro stimulation with at least 50 µg/ml LPS in order to produce the inhibitor according to the invention (TNFI) in good yields ($45 \pm 4.9\%$ inhibition of TNF synthesis, n=5, p<0.026 compared with the LPS control). TNFI obtained from macrophage cultures which have been stimulated with 5 µg/ml LPS reduced the release of TNF from 660 U/ml TNF to $511 \pm 43$ U/ml (=$78 \pm 6\%$ of the control, n=2). The controls have an activity of 660 U/ml TNF.

EXAMPLE 3

Induction of the Inhibitors According to the Invention in Macrophages from C3H/HeJ Mice The LPS low-responder mice of the strain C3H/HeJ (Bomholtgard Ltd., Denmark) are distinguished by a genetically determined LPS tolerance. Peritoneal macrophages were prepared from C3H/HeJ mice and cultivated in vitro with various LPS concentrations (0.5/ µg/ml and 50 µg/ml) for 18 hr ($1 \times 10^6$/ml, 37° C., 8% $CO_2$). The working up was carried out as described for the macrophages from tolerant mice (Example 1).

After the working up, the reconstituted lyophilisates are examined for activity. The TNF secretion by the RAW 264.7 cells stimulated with LPS (200 µg/ml) is 3050 U/ml TNF (control). Table 1 shows that the C3H/HeJ mice produce a small amount of TNFI. The formation of TNFI can be greatly increased by in vitro stimulation with LPS.

TABLE 1

Induction of TNF-inhibitory activity in culture supernatants from C3H/HeJ mice

| Mouse strain | LPS (µg/ml) | Number of cells ($\times 10^6$) | TNF titer in the RAW 264.7 assay (U/ml) |
|---|---|---|---|
| NMRI | 50 | 3.0 | 300 |
| NMRI | 50 | 1.0 | 100 |
| NMRI | 50 | 0.5 | 400 |
| C3H/HeJ | 0 | 3.0 | 2100 |
| C3H/HeJ | 0 | 1.0 | 2300 |
| C3H/HeJ | 0 | 0.5 | 2100 |
| C3H/HeJ | 5 | 3.0 | 800 |
| C3H/HeJ | 5 | 1.0 | 800 |
| C3H/HeJ | 5 | 0.5 | 1100 |
| C3H/HeJ | 50 | 3.0 | 335 |
| C3H/HeJ | 50 | 1.0 | 398 |
| C3H/HeJ | 50 | 0.5 | 335 |

EXAMPLE 4

TNFI from Human Peripheral Monocytes

A volume of 50 ml of blood is taken from two endotoxin-treated human subjects (100 ng of LPS from Salmonella abortus equi/person), in each case 3 days after the treatment, and mononuclear phagocytes (monocytes) are prepared from this. The latter are purified by adherence and stimulated with LPS in serum-free medium (20 h, 50 µg/ml, 37° C., 8% $CO_2$). A crude extract is prepared from the supernatants as described for the mouse macrophages and is assayed for TNFI activity. This is carried out in cultures of human monocutes and in RAW cells which have been stimulated with LPS to synthesize TNF. As is evident from Table 2, partially purified supernatants from LPS-stimulated monocytes from human subjects who are treated with endotoxin (hTNFI) are able to inhibit the synthesis of TNF in cell cultures of human monocytes (hMφ+LPS: $870 \pm 64$ U/ml, hMφ+LPS+hTNFI: $230 \pm 42$ U/ml). If murine TNFI (prepared as described in Example 1) is employed, an inhibition of TNF synthesis to the same extent can be found (hMφ+LPS+mTNFI: $190 \pm 53$ U/ml). On the other hand, hTNFI is also able to block TNF production in mMφ to the same extent as mTNFI (mMφ+LPS:$1026 \pm 132$ U/ml, mMφ+LPS+hTNFI: $98 \pm 24$ U/ml, mMφ+LPS+mTNFI: $134 \pm 16$ U/ml).

It is evident from this that human monocutes from individuals pretreated with endotoxin have been made able to synthesize TNFI, and that hTNF and mTNF cross-react in their biological activity with regard to the inhibition of TNF formation.

TABLE 2

Action of human and murine TNFIS on the TNF synthesis of human monocytes and RAW 264.7 cells

| Incubation | TNF (U/ml) |
|---|---|
| hMφ | 44 + 26 |
| hMφ + LPS | 870 + 64 |
| hMφ + LPS + hTNFI | 230 + 42 |
| hMφ + LPS + mTNFI | 190 + 53 |
| mMφ | 56 + 13 |
| mMφ + LPS | 1026 + 132 |
| mMφ + LPS + hTNFI | 98 + 24 |
| mMφ + LPS + mTNFI | 134 + 16 |

EXAMPLE 5

Purification of TNFI from Peritoneal Macrophages from Mice

The inhibitor-containing supernatant can be concentrated, while retaining the biological activity, by ultrafiltration. Cell culture supernatants from tolerant, LPS-stimulated peritoneal macrophage cultures, prepared as in Example 1 ($1 \times 10^6$/ml, 50 µg/ml S. friedenau, 37° C., 8% $CO_2$) are filtered through a membrane with an exclusion limit of 10 kD. The filtration is stopped as soon as the sample volume has been concentrated to 10% of the initial volume. Retentate and filtrate are sterilized by filtration and 100 µl of retentate or 1 ml of filtrate are assayed for TNFI activity in RAW cell cultures. The biological activity is recovered in the retentate, i.e. those RAW 264.7 cells whose culture medium contains 10% of the concentrated cell culture supernatant secrete after stimulation with LPS only $17.8 \pm 11.5\%$ (n=6) of LPS-stimulated RAW cells, which release $1142 \pm 87$ U/ml TNF (n=6). The inhibitor-containing, concentrated supernatant contains large amounts of lipopolysaccharide, which is removed by affinity chromatography on ®Polymyxin B-agarose (Sigma). 2 ml of Polymyxin B-agarose are placed on the membrane of a 0.2 µm circular filter and washed with 15 ml of pyrogen-free water, and then the LPS-containing retentates are chromatographed with a drop rate of about 1 ml/min. The material obtained after Polymyxin affinity chromatography contains inhibitor activity and inhibits the TNF synthesis by RAW cells by 71% ($1 \times 10^6$ cells, 100 μl of eluate; 200 ng/ml S. friedenau, 18 h, 37° C., 8% $CO_2$).

The chromatography on Polymyxin B-agarose is followed by dialysis against water, which is continued until no phenol red, which is contained in the culture medium, is visible. After this the dialyzed material is freeze-dried. The lyophilized material contains the inhibitory activity. The lyophilisate reconstituted in fresh medium was able to reduce the production of TNF in RAW cells to 18±6% (n=5) of the LPS-stimulated controls (p<0.009).

The TNFI-containing material is further purified by chromatography on Sephadex S-200 gel (phosphate buffer 0.5 mmol/e+0.2 mol/e NaCl, 3 ml/h).

The biological activity is essentially found in fraction 6: even 100 μl (corresponding to 10% of the total volume) were able to bring about approximately 86% inhibition of TNF release (RAW 264.7 $1 \times 10^6$+200 ng/ml LPS: 1149 U/ml TNF; RAW 264.7, $1 \times 10^6$+200 ng/ml LPS +100 μl TNFI: 152 U/ml TNF). Comparative SDS gel electrophoresis reveals a molecular weight of 40,000 to 80,000.

EXAMPLE 6

Inhibition of TNF Synthesis Induced by Phorbol Ester

TNF synthesis is induced by a combination of phorbol ester (PMA) and interferon (IFN-γ; Amersham, Germany). RAW 264.7 cells ($1 \times 10^6$/ml) were incubated with LPS (10 μg/ml) and interferon-γ (50 U/ml) and with various concentrations of phorbol ester (500 ng/ml, 100 ng/ml and 20 ng/ml) in combination with interferon-γ (50 U/ml) (18 h, 37° C., 8% $CO_2$). The RAW 264.7 cells produce TNF both after stimulation with LPS/interferon-γ and incubation with PMA/interferon-γ (LPS/IFN-γ: 2450±274 U/ml TNF=100%, n=4; 500 ng/ml PMA/50 U/ml IFN-γ:1460±60 U/ml TNF (n=2),=60±2.5% of the amount inducible by LPS/IFN-γ). The amount of TNF inducible by PMA-/IFN-γ is dose-dependent: 1140±213 U/ml (=47±8.6% of the LPS/IFN-γ control, n=2) were released by 100 ng/ml PMA/50 U/mi IFNγ; 20 ng/ml PMA/50 U/ml IFN-γ result in the secretion of 680±164 U/ml TNF (=28±7% of the LPS/IFN-γ control).

To investigate the effect of TNFI on the PMA/IFN-induced TNF formation, RAW cells are incubated with PMA/IFN-γ in the presence of inhibitor ($1 \times 10^6$/ml; 18 h,, 37° C., 8% $CO_2$). The inhibitor according to the invention inhibits both LPS/IFN-γ- and PMA/IFN-γ-induced TNF synthesis and release. The amount of inhibitor which inhibits the LPS/IFN-γ-induced TNF release by about 70% to 29±6% (n=2; p<0.08) of the LPS control inhibits the PMA/IFN-γ-stimulated TNF release by about 90% to 10±4%, to 40 U/ml TNF (n=5, p<0.04).

EXAMPLE 7

Inhibition of TNF Synthesis in Thioglycolate-Induced Peritoneal Macrophages

Thioglycolate-induced peritoneal macrophages are incubated with LPS and various amounts of inhibitor for 18 h ($1 \times 10^6$/ml; 200 ng/ml LPS; 37° C., 8% $CO_2$).

The amounts of inhibitor employed correspond to the amounts which secrete $1 \times 10^7$/ml (=TNFI 1), $5 \times 10^6$/ml (=TNFI 2), $2.5 \times 10^6$/ml (=TNFI 3) and $5 \times 10^5$/ml (=TNFI 4) peritoneal macrophages from tolerant mice. Also used in these experiments are lyophilisates, reconstituted in culture medium, from supernatants of LPS-stimulated peritoneal macrophages from tolerant mice. LPS induced TNF (6700 U/ml=100%) in these cells. Under the influence of inhibitor, the amount of TNF detectable in the culture supernatant decreases as a function of the amount of inhibitor employed: the concentration in the mixture TNFI 1 and that in TNFI 2 was able to suppress TNF release to <40 U/ml (<1% of the LPS control, n=4; p<0.04). The product from $2.5 \times 10^6$ peritoneal macrophages brings about a reduction in TNF formation to 1440±100 U/ml TNF (corresponding to 21±1.4%, n=2; p>0.15); $5 \times 10^5$ peritoneal macrophage product were still able to reduce the TNF release to 34±4.6% (2260±310 U/ml TNF; p>0.22).

EXAMPLE 8

TNFI Has No IL 6 Activity

An aliquot of the fraction 6 containing TNFI activity after chromatography on G 200 from Example 5 is examined to find whether it contains the biological activity of interleukin 6 (IL 6). The volume which inhibits the synthesis of TNF by about 70% in the RAW cell assay is employed. This volume is incubated in a serial dilution (1:2) with cells of the hybridoma cell line B 13.29 (obtained from Dr. L. Aarden, Central Laboratory Blood Transfusion Service, P.O. Box 9406, 1006 AK Amsterdam, Netherlands) in 96-well microtiter plates in addition to 100 μl of cell culture medium (Iscove's medium containing BSA, transferrin, soybean lipids, β-mercaptoethanol; ready-to-use solutions from Boehringer, Mannheim) at 37° C. and 8% $CO_2$ for 48 h. Used as controls are B 13.29 cultures which are treated with a series of concentrations of recombinant IL 6 (IC Chemikalien, Munich). The staining and quantification of the cells is carried out as in Example 1. The absolute content of IL 6 can be determined by comparison with the series of IL 6 concentrations. It emerges that the B13.29 cells are not stimulated to grow by the fraction, containing the TNFI activity, from the macrophage supernatant, which is the case in cultures to which recombinant IL 6 is added. It is evident from this that the tested aliquot contains no IL 6 and that TNFI is not IL 6.

I claim:

1. An inhibitor of the formation of tumor necrosis factor which has a molecular weight of from 40,000 to 80,000 obtainable by cultivation of macrophages or mononuclear phagocytes from lipopolysaccharide-tolerant vertebrates.

2. An inhibitor as claimed in claim 1, obtainable by cultivation of macrophages from lipopolysaccharide-tolerant mice.

3. An inhibitor as claimed in claim 1, obtainable by cultivation of mononuclear phagocytes from lipopolysaccharide-tolerant humans.

* * * * *